United States Patent [19]
Forney

[11] Patent Number: 5,373,859
[45] Date of Patent: Dec. 20, 1994

[54] TONGUE POSITIONING DEVICE

[76] Inventor: LeRoy S. Forney, 313 S. 17th St., Apt. 3F, Philadelphia, Pa. 19103

[21] Appl. No.: 49,182

[22] Filed: Apr. 19, 1993

[51] Int. Cl.⁵ .................... A61F 5/37; A61C 5/14
[52] U.S. Cl. ........................... 128/846; 128/860
[58] Field of Search ............... 128/848, 859–862, 128/62 A; 604/181, 77

[56] References Cited

U.S. PATENT DOCUMENTS

| | | | |
|---|---|---|---|
| 374,122 | 11/1887 | Genese | 128/15 |
| 480,787 | 8/1892 | Scott | 604/77 |
| 625,879 | 5/1899 | Gardner . | |
| 779,360 | 1/1905 | Grummann . | |
| 2,178,128 | 10/1939 | Waite | 128/136 |
| 2,521,084 | 9/1950 | Oberto | 128/141 |
| 2,589,504 | 3/1952 | Miller | 128/136 |
| 3,211,143 | 10/1965 | Grossberg | 128/136 |
| 3,224,442 | 12/1965 | Stubbs | 128/136 |
| 3,312,216 | 4/1967 | Wallshein | 128/136 |
| 3,312,217 | 4/1967 | McKinstry | 128/136 |
| 3,387,610 | 6/1968 | Richmond | 604/216 |
| 3,434,470 | 3/1969 | Strickland | 128/136 |
| 3,448,738 | 6/1969 | Berghash | 128/136 |
| 3,513,835 | 5/1970 | DeCeuster | 128/12 |
| 3,616,497 | 11/1971 | Esposito, Jr. | 24/81 HS |
| 3,809,094 | 5/1974 | Cook | 128/321 |
| 3,864,832 | 2/1975 | Carlson | 32/40 R |
| 3,946,736 | 3/1976 | Neward | 604/181 |
| 4,112,951 | 9/1978 | Hulka et al. | 128/346 |
| 4,169,473 | 10/1979 | Samelson | 128/136 |
| 4,170,230 | 10/1979 | Nelson | 128/139 |
| 4,196,724 | 4/1980 | Wirt et al. | 128/136 |
| 4,198,967 | 4/1980 | Dror | 128/136 |
| 4,262,666 | 4/1981 | Nelson | 128/203.23 |
| 4,304,227 | 12/1981 | Samelson | 128/136 |
| 4,471,771 | 9/1984 | Steven et al. | 128/136 |
| 4,516,936 | 5/1985 | Hulsink | 433/6 |
| 4,519,386 | 5/1985 | Sullivan | 128/136 |
| 4,593,686 | 6/1986 | Lloyd et al. | 128/136 |
| 4,669,459 | 6/1987 | Spiewak et al. | 128/136 |
| 4,676,240 | 6/1987 | Gardy | 128/207.14 |
| 5,046,512 | 9/1991 | Murchie | 128/848 |
| 5,154,184 | 10/1992 | Alvarez | 128/848 |

FOREIGN PATENT DOCUMENTS

| | | |
|---|---|---|
| 65194 | 2/1892 | Germany . |
| 2704709.2 | 2/1977 | Germany . |

OTHER PUBLICATIONS

Lowe, Alan A., DMD, PhD, FRCD(C), "Dental Appliances for the Treatment of Snoring and/or Obstructive Sleep Apnea," *Principles and Practices of Sleep Medicine*, 2nd Ed. (Kruger et al., Ed.) (W. D. Saunders, 1993) (in press).

Ortiz, P. J., "Aquadilla Man Invents Device to Stop Snoring," San Juan Star (vol. No. 107), Feb. 18, 1992.

*Primary Examiner*—Michael A. Brown
*Attorney, Agent, or Firm*—Woodcock Washburn Kurtz Mackiewicz & Norris

[57] ABSTRACT

A device is provided to retain the tongue in a normal or extended position without undue discomfort for an extended period of time by holding the tongue securely in a housing by means of vacuum created within the device. The housing may then be positioned by holding it with the fingers or, in another embodiment, by an integral flange which rests against the face and permits self-application. The device uses a housing that is designed to form a seal with the tongue at its proximal portion, and diverging walls within the housing to limit other areas of contact with the tongue. The device also preferably uses an opening that is arcuate shaped and includes a soft conformable extension portion. Certain embodiments of the device disclosed are particularly adapted to control snoring by preventing the tongue from blocking the airway. Embodiments using a separate tongue receiver connected to a remote control unit that may include a vacuum supply are also disclosed.

22 Claims, 3 Drawing Sheets

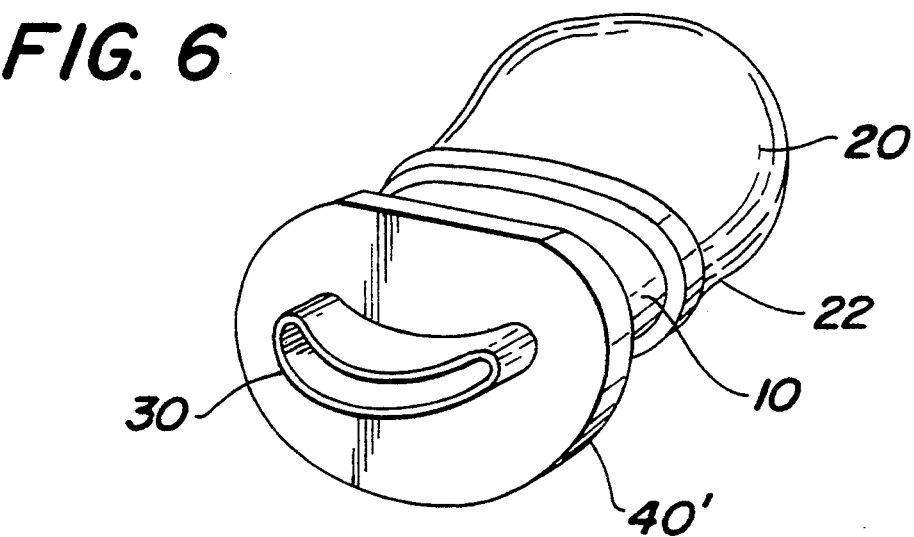
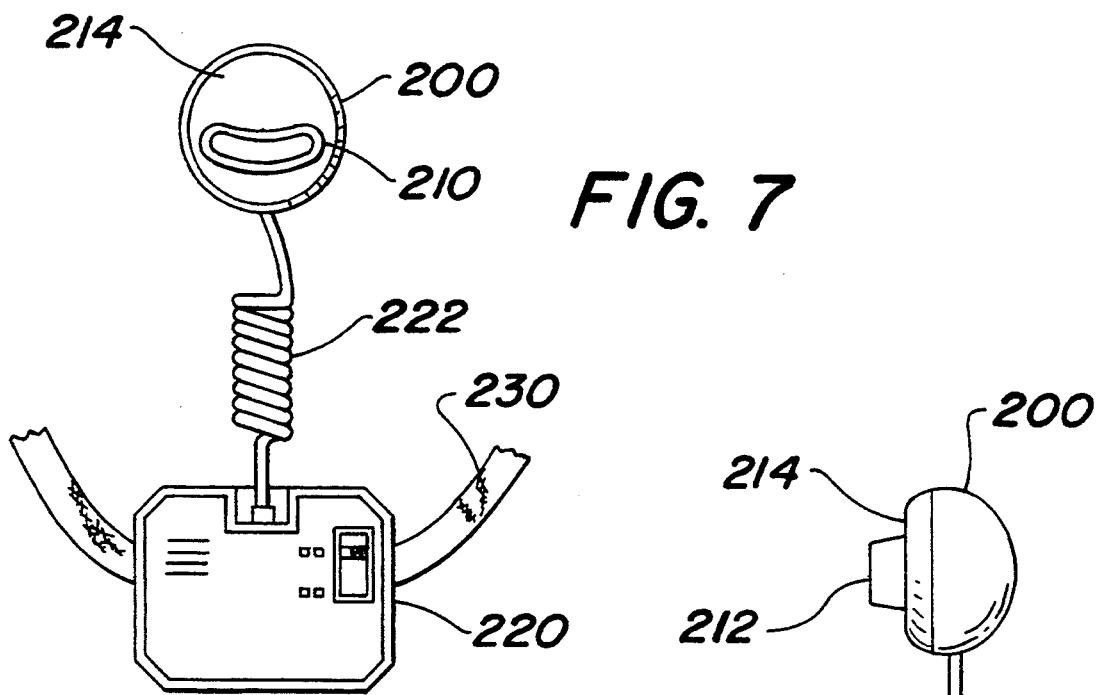
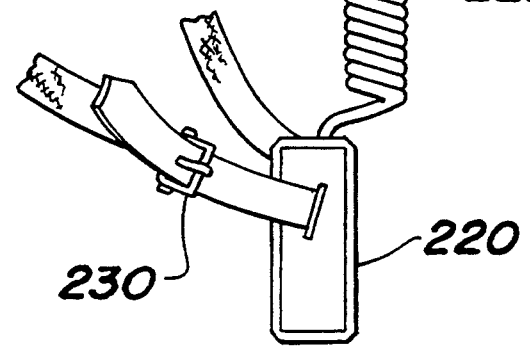

TONGUE POSITIONING DEVICE

The present invention relates to devices for positioning and restraining the tongue of a subject and also relates to preventing the tongue from falling back into the throat during sleep, and thereby causing sonorous respiration (snoring) and, potentially, sleep apnea.

BACKGROUND OF THE INVENTION

For a variety of reasons, medical practitioners often need to hold the tongue of a patient either in a fixed position or must manipulate the tongue to facilitate access to a portion of the oral cavity. Additionally, it is known that sonorous respiration (snoring) occurs while breathing through the mouth during sleep when the tongue partially blocks the airway. Thus, one way to cure or mitigate snoring is to hold the tongue in a forward position, whereby airway blockage cannot occur. Although generally merely an annoyance to those other than the person snoring, it is known that in certain instances airway blockage will become complete resulting in apnea, i.e., a cutting off of the air supply to the lungs and thus decreasing the amount of oxygen carried by the blood to the brain. Sleep apnea can cause disruptive sleep patterns, resulting in chronic fatigue, and can cumulatively cause brain damage. Therefore, for many patients, reducing or eliminating snoring is a serious matter.

Many types of tongue holding devices are known. For example, metallic or hard plastic clips are disclosed in the art, e.g., in U.S. Pat. No. 4,198,967—Dror and U.S. Pat. No. 3,809,094—Crook. However, these devices risk pain and injury to the tongue, and are particularly unsuited to self-administration. A less traumatic device designed for self-administration and for extended periods of use (i.e., overnight) is disclosed in U.S. Pat. Nos. 4,169,473 and 4,304,277, both to Samelson. The device disclosed in the Samelson patents evacuates air from a tongue holder and uses an imperforate structure in a device that is positioned by holding both dental arches in a locked position. Such a device, however, is detrimental to the normal bite relationship of the dental arches since it distorts the relationship of the upper and lower jaws.

U.S. Pat. No. 4,196,724—Wirt discloses a tongue receptacle having a rearwardly converging configuration into which the tip of the tongue is wedged. However, the device disclosed in the Wirt patent causes pain, swelling and edema by concentrating an applied vacuum to a small area of the tip of the tongue. Furthermore, the requirement for an attachment to a vacuum-producing device such as the disclosed elastically contractible bellows is cumbersome and annoying to a sleeping user.

U.S. Pat. No. 4,676,240—Gardy proposes a device that engages either the teeth or the gum arches to anchor the device in position. The tongue is received in a vacuum chamber and displaces the air therein. The tongue is sealed in the chamber by internal sealing ridges located on the inside of the vacuum chamber.

There remains, however, a need for a simple and reliable device that can comfortably restrain the tongue in a predetermined position. It is therefore an object of the present invention to provide a simple, compact means for creating vacuum to hold the tongue which does not encumber the subject using the device. It is another object of this invention to prevent undue discomfort to the subject by providing means whereby a vacuum is applied to cause the device to sealingly engage a large portion of the tongue and in which the seal is designed to prevent inadvertent loss of vacuum through normal tongue movements, contractions and contortions, even during sleep. It is further desired that these features acting alone or together permit a decrease in the vacuum required to hold the tongue securely in the device, thereby decreasing the discomfort associated with use of the device.

SUMMARY OF THE INVENTION

Accordingly, it has now been found that these and other objects can be attained by providing a device adapted for insertion into the mouth of a subject for holding the tongue. The device of the present invention includes a housing having an opening at one end, and walls that preferably diverge as they move away from the opening, thereby containing the tongue without substantially contacting it or impinging upon it except at the open end of the housing into which the tongue is inserted. The opening itself is most preferably arcuate shaped and compliant so as to form a conforming seal with the tongue, thereby accommodating a wide range of contractions, contortions and movements of the tongue without disrupting the vacuum seal. The opposite end of the housing is closed, and serves as a vacuum reservoir which is preferably activated by squeezing, thereby drawing the tongue into the housing and holding it comfortably and securely. In this manner, the vacuum may be generated by the vacuum reservoir or may be supplied by an external vacuum source connected to the housing.

In use, the present invention retains the tongue securely in the device by vacuum, and thus the tongue may be positioned as needed by holding the housing with the fingers, as required for examination of a patient. Embodiments of the invention are also discoursed, however, that are of special value in the treatment of snoring and obstructive sleep apnea. These embodiments include a flange attached to the housing to position the housing by contacting the subject's face, thereby maintaining the tongue in either a normal or an extended position. These embodiments facilitate self-application, and also serve to prevent the tongue from falling backward during sleep to cause snoring and obstructive apnea.

BRIEF DESCRIPTION OF THE DRAWINGS

FIG. 6 is a perspective view of another embodiment of the present invention.

FIG. 7 is a front view of another embodiment of apparatus made in accordance with the present invention that uses a remote source of vacuum.

FIG. 8 is a side view of the apparatus depicted in FIG. 7.

DETAILED DESCRIPTION OF THE INVENTION

The present invention discloses tongue holding devices for subjects under the effects of anesthesia, when unconscious, in a coma, asleep, or when medical or dental work is being done in the mouth or throat and control over the tongue is required. However, the devices disclosed herein are also useful for reducing or eliminating the occurrence of snoring and related apneic episodes. Thus, as used herein, the term "subject" refers to any user of the present invention, whether such use is by a physician or other practitioner, or by self-administration.

The basic principle of the present Invention is the creation of a vacuum within a chamber that is sealed against the tongue. As used herein "vacuum" denotes the creation of either a static or dynamic condition of lower pressure. Those of skill in the art will appreciate that the exact degree of such a vacuum is readily determined empirically and is governed by the material properties and surface finish of the materials that comprise the housing, as well as the shape of the housing itself.

Figure 1:
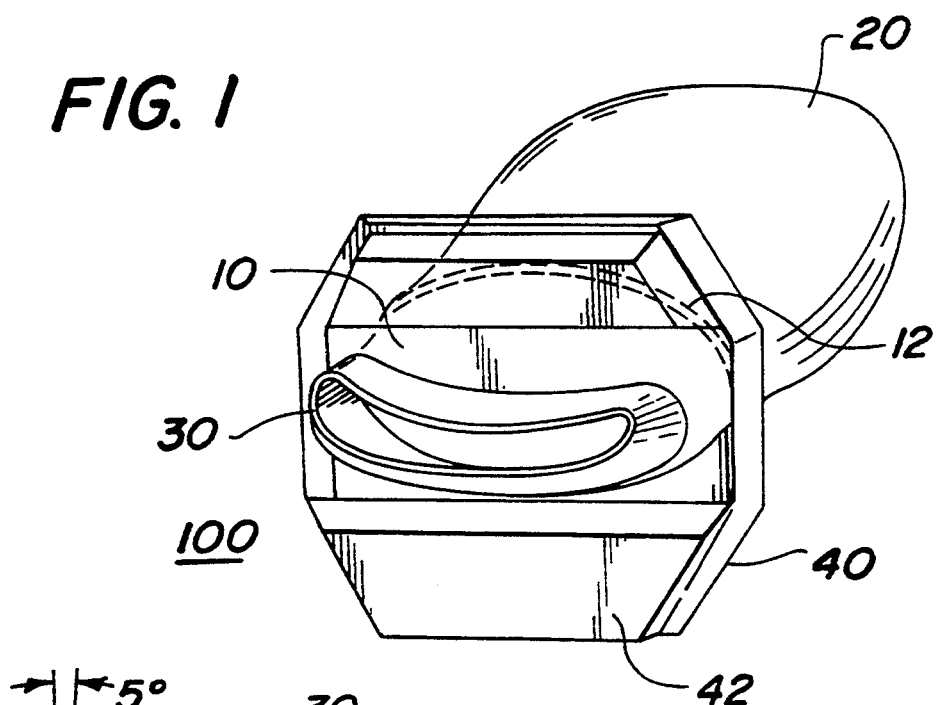
FIG. 1 is a perspective view of an embodiment of the present invention.

As seen in FIG. 1, a preferred embodiment of the device 100 of the present invention includes a housing 10 to receive the tongue. The housing 10 is preferably a relatively rigid, elongated, tubular structure, with a closed flexible vacuum reservoir 20 connected to or forming a distal end of the housing 10 and a flexible seal opening 30 disposed at a proximal end that preferably divergingly tapers from an opening in the housing 10 to receive the tongue. In certain embodiments, a flange 40 is attached to the housing 10 to maintain the tongue in an extended position by contacting the face of the subject, as explained in further detail below.

Figure 1A:
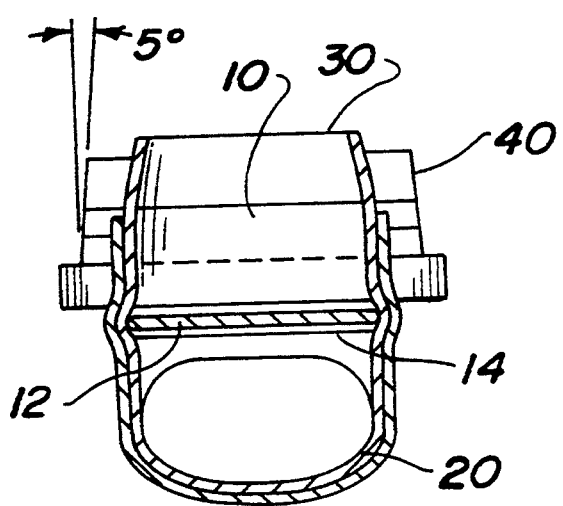
FIG. 1A is a cross-sectional top plan view taken along line A—A shown in FIG. 2.
Figure 2:
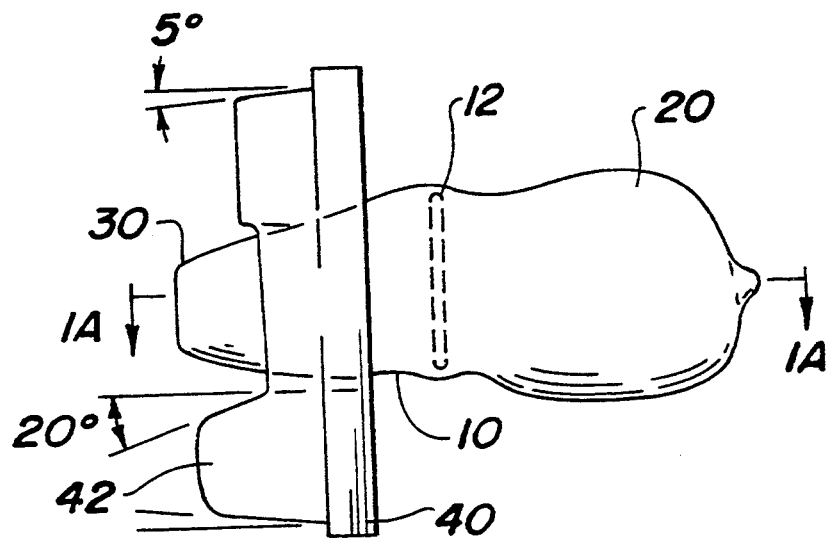
FIG. 2 is a side elevation view of the embodiment of the present invention shown in FIG. 1.
Figure 3:
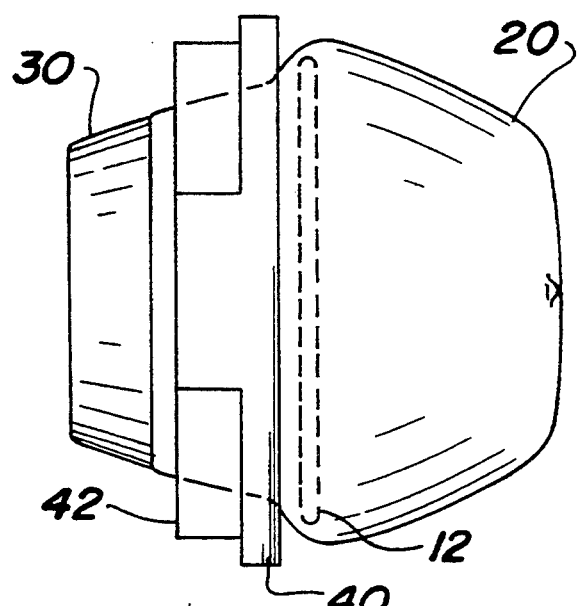
FIG. 3 is a top plan view of a the embodiment the present invention shown in FIG. 1.

The housing 10 is preferably constructed of either a rigid material or of a flexible material rendered rigid by the incorporation of supporting members, one of which may be the flange 40. An internal supporting member 12 disposed inside the housing 10 is also used in certain embodiments, and is shown in phantom in FIG. 1. Referring now to FIG. 1A, there is shown a cross-sectional top plan view of the device 100 shown in FIG. 1. In this view, it can be seen that the housing 10 is preferably molded as a one piece unit using a flexible material. The internal supporting member 12 is also visible. The internal supporting member 12 is preferably comprised of a material having greater rigidity than the housing 10, and is most preferably a flexible metallic element, for example, a section of spring wire constrained by a slot 14. As seen in FIG. 1A and FIGS. 2-3, the housing 10 preferably has a cross-sectional area greater than that of the seal opening 30 to ensure that the tongue is not wedged or squeezed as it extends into the housing 10. In other words, if the seal opening 30 is defined as the proximal end of the device, a cross-section taken immediately distal of the proximal end increases with the distance from the seal opening, i.e., the side walls diverge. In a preferred embodiment of the device of the present invention, the cross-section of the proximal end of the seal opening 30 is also comprised of a compliant material whose cross-section at the open end is smaller than the cross-section where it joins the housing 10.

As seen in FIG. 1, the cross-section of the seal opening 30 describes an arcuate shape having opposing convex and concave walls. The cross-section of the proximal end of the housing 10 at the union with the seal opening 30, or that forms the seal opening 30, most preferably also describes such an arcuate shape. It will be understood, therefore, that in those embodiments in which the housing 10 and the seal opening 30 are two separate components that the proximal end of the housing 10 that joins the distal end of the seal opening 30 is arcuate in cross-section. However, in those embodiments where the seal opening 30 is integrally formed with the rest of the housing 10, the arcuate opening begins at the proximal end of the seal opening 30 as seen in FIG. 1, and continues in the distal direction for a distance sufficient to accommodate the tongue, preferably between about one-half to one and one-half inches. As will be appreciated from FIGS. 2-3, however, it will be difficult in certain embodiments to discern the transition between the seal opening 30, the housing 10 and the vacuum reservoir 20, the latter being connected to the distal end of the housing 10. Additionally, in certain embodiments, a two piece device is provided in which the vacuum reservoir 20 also serves the function provided by the housing 10 of maintaining an arcuate opening in the seal opening 30 and preventing the tongue from being squeezed or wedged when inserted into the device 100. Finally, in certain embodiments, the seal opening 30 and surrounding sealing material, the housing 10 and the vacuum reservoir 20 are all molded or formed to make an integral, one piece device in accordance with the present invention.

It will be appreciated that the vacuum reservoir 20 is constructed of a flexible material and is of a stiffness and design such that it may be squeezed to create a vacuum sufficient to pull the tongue into the housing 10 but not so great as to cause injury or pain to the tongue. As shown in FIG. 1A, this is preferably accomplished by choosing the material and the wall thickness of the housing to partially provide these characteristics, and then providing an overlying layer of material 22 to add stiffness while retaining some flexibility, thereby providing sufficient vacuum. Although the housing 10 is preferably formed from a rigid material to maintain its shape, in certain preferred embodiments, the housing 10 is formed from a semi-rigid material and shape is maintained by one or more internal or external support members. By careful control of the rigidity of the housing 10, the degree of vacuum created by squeezing the vacuum reservoir 20 that forms or is connected to the closed end of the housing 10 may be controlled. As noted, in some embodiments, the housing 10 and flexible vacuum reservoir 20 can be formed as an integral unit and, in alternate embodiments., the housing 10 and the sealing portion 30 are formed as an integral unit, or, finally, all three elements are combined into a unitary structure.

In certain embodiments, the housing 10, seal opening 30 and vacuum reservoir 20 alone will create a useful device that can be used to hold and manipulate the tongue during medical procedures. However, as mentioned above, a tongue positioning device such as that disclosed herein can itself also be used to hold the tongue in a fixed position. Such embodiments are also useful during medical procedures, for example to prevent the tongue from blocking the airway during the administration of anesthesia. Additionally, as explained above, if the tongue can be held in a slightly forward position during sleep, the chances of snoring and/or of sleep apnea, are dramatically lessened. Thus, referring again to FIGS. 1-3, a flange 40 is preferably provided in such embodiments. The flange 40 is attached to the exterior of the housing 10 and is of sufficient size to not easily slip through the lips or teeth of a subject. As used herein the term "flange" denotes any structure that extends laterally from the exterior surface of the housing 10. In the embodiment of the present invention depicted in FIG. 1A, the flange 40 has surfaces that are either parallel to the surface which contacts the housing 10 or, preferably, at an angle to that which contacts the housing 10. For example, in a preferred embodiment, these two surfaces are at an angle of about 5° to each other, as shown in FIG. 1A. In similar fashion, the angle of the outer and inner surfaces of the flange 40 seen in FIG. 2 are preferably at angles of about 5° and 20°, respectively, relative to the sides of the housing 10, as shown.

Figure 4:
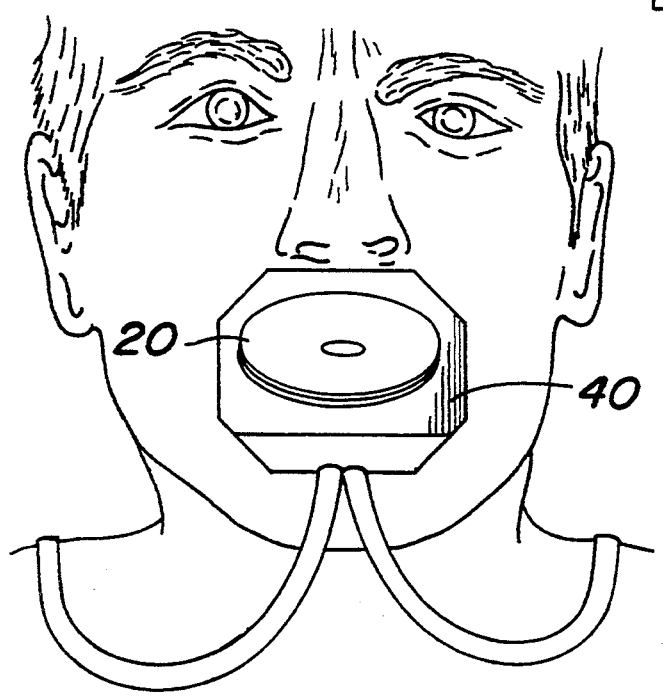
FIG. 4 is an end elevation view of the embodiment of the present invention shown in FIGS. 1-3 placed in the mouth of a subject.
Figure 5:
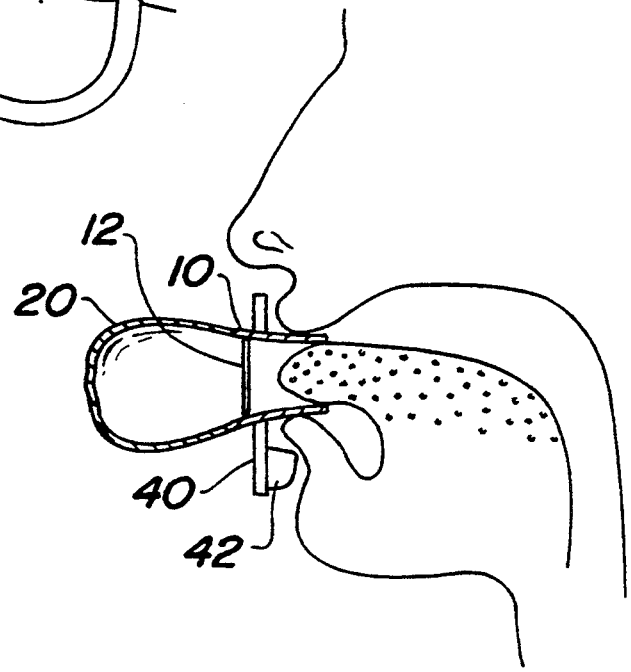
FIG. 5 is a side elevation view, partially in cross-section, of the embodiment of the present invention shown in FIGS. 1-3, shown in use as in FIG. 4.

The flange 40 is preferably molded from a thin sheet of material and is therefore provided with a peripheral wall for strength, as shown. As explained below and seen in FIG. 2, a projection 42 is preferably provided to conform to the facial contour of a typical subject. Referring now to FIG. 4, the embodiment of the device illustrated in FIGS. 1–3 is shown in use. In order to position the device, the vacuum reservoir 20 is squeezed to evacuate most of the air and the tongue is inserted into the housing 10, as seen in cross-section in FIG. 5. Upon release of the squeezing force, the sidewalls of the vacuum reservoir 20 tend to return to their original position, but are precluded from doing so since the seal between the surface of the tongue and the seal opening 30 prevents sufficient air from re-entering the interior of the vacuum reservoir 20. Thus, a vacuum is created and the tongue is retained. However, in order to retain the tongue in a particular position, such as either a normal or an extended position, it is necessary to provide a fixed point relative to the tongue positioning device. As explained above, this is preferably accomplished by the flange 40, shown in FIGS. 1–3. As seen in FIG. 4, the flange is most preferably sized to extend from beneath the patient's nose to the chin area, thereby partially covering the mouth. The flange 40 rests against the face of the subject, i.e., against the lips, teeth and/or surrounding tissue. As mentioned above and seen in FIG. 5, the flange 40 most preferably includes a projection 42 that extends proximally and engages the chin and lower lip to help hold the flange 40 in place.

Another preferred embodiment of the present invention is illustrated in FIG. 6. This embodiment allows convenient operation to gain control of the tongue and its position. In this case, the flange 40 described above that positions the housing 10 is a simple collar 40' cut from a flat plate of rigid material. The purpose of the collar 40' is to stabilize the shape of the opening in the housing 10 without obstructing access to the oral cavity, while maintaining the arcuate cross-sectional shape of the seal opening 30, which, as pointed out above, is advantageous for accommodating normal movements of the tongue without breaking the vacuum seal. The collar 40' also functions as the flange 40 described above to position the device 100 by resting against the face, and thus holds the tongue in a particular position. Additionally, this embodiment of the invention illustrates the use of an external support member 22 that replaces the internal support 12 described above.

Referring now to FIGS. 7–8, an alternate embodiment of the apparatus of the present invention is depicted. In some instances, it will be desirable to provide a vacuum using a source other than the vacuum reservoir described above. For example, it may be necessary to reduce the size of the device so that the tongue can be manipulated or to leave room for access to the oral cavity. In some instances it may be required to precisely maintain the amount of vacuum applied to the tongue. As seen in FIG. 7, in this embodiment, a tongue receiver 200 is provided that preferably has an arcuate opening 210, as described above. The housing 200 is connected to a vacuum source preferably contained within a control unit 220 by a flexible vacuum tube 222. The control unit is most preferably a battery powered unit. As known to those of ordinary skill, such a unit may include electronic circuits that permit the level of vacuum to be sensed and regulated, and may also, provide an audible alarm if the vacuum is removed or the tongue receiver 200 becomes detached from the subject. The control unit 220 most preferably includes a pump and pressure sensor, an alarm, a target pressure adjustment and a power source and power level warning if a battery operated unit is provided. It will be understood, however, that numerous; combinations of these features may be provided. For example, the control unit does not necessarily have to contain the vacuum source, since either an additional external source that is connected to a remote vacuum pump could be connected to the tongue receiver 100 or the flexible vacuum reservoir described above could be used. In these embodiments, the control unit would therefore function as a monitor, and the vacuum tube 220 would act as a sensing port, rather than the conduit to draw a vacuum.

As shown in FIG. 8, the tongue receiver 200 preferably includes a soft flexible extension 212 that extends from the flange or face plate 214 shown. The face plate 214 provides the same function as the flange 40 or plate 40' described above by contacting the face of the subject to resist the withdrawal of the tongue into the mouth. A strap 230 is preferably included to keep the control unit 220 in place. The tongue receiver 200 is preferably comprised of a rigid material in this embodiment and diverges from the tongue surface as described above so that the formation of the seal is limited to the region around the opening 210 in the tongue receiver 200, most preferably including the extension 212.

The embodiment of the present invention depicted in FIGS. 7–8 is useful for controlling snoring or sleep apnea since the alarm will awaken the subject when the tongue slips from the tongue receiver 200. Additionally, this embodiment is useful since it provides a patient monitoring function that would be helpful during the administration of cardiopulmonary resuscitation (CPR); while treating an epileptic or comatose subject; during oral, or ear nose and throat surgery; or during other surgery while the patient is either under anesthesia or recovering from the effects of anesthesia. In use, the tongue is inserted into the tongue receiver and the vacuum source is activated. The device creates and maintains a preset vacuum pressure and preferably sounds an alarm if the device is detached or cannot maintain the predetermined pressure level.

In any embodiment, the present invention generally encompasses two particular features that aid in providing a useful and comfortable device. First, the housing 10 is designed so that it does not substantially constrain the tongue except at the point of entry into the device. This is important to the operation of the present invention as it allows vacuum to be applied to the greatest portion of the tongue, thereby minimizing swelling or edema which occurs if vacuum is applied only to a small portion of the tongue. This lack of constraint is accomplished in several ways in different embodiments. For example, the housing 10 is provided with internal (FIGS. 1–3) or external (FIG. 6) support members to prevent the collapse of the housing 10 against the tongue. Moreover, the walls of the housing 10 are designed to diverge from the opening, and the housing 10 itself is preferably constructed of a rigid or semi-rigid material to restrict its collapse under negative pressure. Finally, the opening of the housing 10 adjacent the seal opening 30 is supported by a flange 40 or similar structure to prevent distortion of the shape of the seal opening 30.

Second, in preferred embodiments, the cross-section of the opening in the housing 10 and the seal opening 30 is arcuate in cross-section, i.e., the lower surface of the opening is convex while the upper surface of the opening is concave. This feature is important for maintaining vacuum and sealing engagement with the tongue through a wide range of contractions, contortions and movements of the tongue.

Third, the housing 10 most preferably opens directly into a vacuum reservoir 20 which is not separated from the housing 10 by a conduit, tube or restriction of any kind. This feature permits minimization of the overall dimensions of the device and gives it sufficient rigidity to resist collapse or dislodging while in normal use. Additionally, the vacuum seal is provided by a flexible, elastic extension of the housing which forms the seal opening that impinges on the tongue, however, as noted above it is preferred that the walls of the seal opening also diverge. The divergent walls prohibit unduly increasing the degree to which the tongue is "wedged" in the device. The tongue is held in an extended position by a flange which engages the face of the subject and thus prevents the device and the tongue from moving rearward.

The foregoing description of certain preferred embodiments is set forth for the purpose of illustrating the principles of the invention. Since numerous alternate uses, modifications and changes will readily occur to those skilled in the art, it is not desired to limit the invention to the exact construction and operation shown and described above. Thus, all suitable modifications and equivalents that may be resorted to will fall within the scope of the invention, which is defined by the appended claims.

What is claimed is:

1. Apparatus for restraining a tongue, comprising a housing connected to a vacuum source, the housing having an opening for receiving the tongue, the opening having walls diverging away from the opening, wherein a cross-section of the housing at a point distal from the opening is larger than the opening, whereby upon application of a vacuum to the housing, a sealing engagement is formed between the tongue and the housing only in a region surrounding the opening.

2. The apparatus of claim 1 further comprising a flange for supporting the apparatus against a subject's face, wherein the flange prevents withdrawal of the tongue into a retracted position.

3. The apparatus of claim 1, wherein the housing further comprises a support member for resisting collapse of the housing.

4. The apparatus of claim 1, wherein the vacuum source comprises a vacuum reservoir, and a vacuum is applied by squeezing the reservoir, inserting the tongue in the opening, and releasing the reservoir.

5. The apparatus of claim 1, wherein the vacuum source comprises a remote vacuum source connected to the housing.

6. The apparatus of claim 1, wherein the opening defines an arcuate opening.

7. The apparatus of claim 1, wherein the opening comprises a soft, deformable extension.

8. The apparatus of claim 7, wherein the extension defines an arcuate extension opening.

9. The apparatus of claim 2, wherein the flange is comprised of one or more surfaces adjacent the opening that contact a wearer's face in the vicinity of the mouth and lips.

10. Apparatus for preventing snoring comprising:
a housing comprising:
a proximal opening for receiving a tongue,
a distal end; and
walls connecting the proximal opening and the distal end, the walls diverging away from the proximal opening, wherein a cross-section of the housing at a point distal from the opening is larger than the opening;
a vacuum source connected to the housing; and
a flange for supporting the apparatus against a subject's face,
whereby upon application of a vacuum to the housing, a sealing engagement is formed between the tongue and the housing, and the flange prevents withdrawal of the tongue into a retracted position by engaging the face.

11. The apparatus of claim 10, further comprising a flexible extension having a proximal opening and an opening at a distal end the distal end of the extension being joined to the proximal opening of the housing, wherein the proximal opening in the extension is smaller than the opening at the distal end of the extension.

12. Apparatus for controlling the position of a tongue comprising: a housing comprising an arcuate opening to receive the tongue on a proximal end of the housing; and a vacuum source connected to the housing, whereby a vacuum seal is created between the tongue and the housing to prevent withdrawal of the tongue from the housing.

13. The apparatus of claim 12 wherein the vacuum source comprises a vacuum reservoir integral with the housing, whereby the vacuum seal is created by squeezing the closed end of the device.

14. The apparatus of claim 12 wherein the vacuum source comprises an external vacuum source, whereby the vacuum seal is created by activating the vacuum source.

15. The apparatus of claim 12 wherein the device further comprises a flange affixed to the housing which contacts a portion of a subject.

16. The apparatus of claim 12 wherein the housing comprises walls that diverge away from the arcuate opening, whereby a cross-section of the housing at the distal end is larger than a cross-section at the proximal end.

17. The device of claim 12 wherein the housing further comprises an external support member, whereby the housing does not collapse sufficiently to impinge upon the tongue to create a vacuum seal between the housing and the tongue.

18. The device of claim 12 wherein the housing further comprises an internal support member, such that housing does not collapse sufficiently to impinge upon the tongue upon the creation of a vacuum seal between the housing and the tongue.

19. The apparatus of claim 12, further comprising a flange affixed to the housing for contacting the face of a subject upon insertion of the tongue into the arcuate opening.

20. The apparatus of claim 19, wherein the flange comprises one or more projections for contacting the face.

21. A method of restraining a tongue comprising the steps of:
    inserting a portion of the tongue into a housing having an opening and walls diverging away from the opening, the housing connected to a vacuum source;
    activating the vacuum source to cause a region surrounding the opening to form a seal with the tongue;
    simultaneously precluding the walls from forming a seal with the tongue except in the region surrounding the opening; and
    supporting the tongue and housing in a position on a user's face.

22. The method of claim 21, wherein the step of supporting the tongue comprises placing a flange connected to the housing against a subject's face.

* * * * *